(12) United States Patent
Jessop et al.

(10) Patent No.: US 10,021,351 B2
(45) Date of Patent: Jul. 10, 2018

(54) STEREOSCOPIC VIDEO IMAGING

(71) Applicant: Ultradent Products, Inc., South Jordan, UT (US)

(72) Inventors: Neil T. Jessop, Sandy, UT (US); Matthew Michael Fisher, Kaysville, UT (US)

(73) Assignee: Ultradent Products, Inc., South Jordan, UT (US)

(*) Notice: Subject to any disclaimer, the term of this patent is extended or adjusted under 35 U.S.C. 154(b) by 134 days.

(21) Appl. No.: 14/403,285

(22) PCT Filed: Mar. 5, 2013

(86) PCT No.: PCT/US2013/029042
§ 371 (c)(1),
(2) Date: Nov. 24, 2014

(87) PCT Pub. No.: WO2013/180773
PCT Pub. Date: Dec. 5, 2013

(65) Prior Publication Data
US 2015/0156461 A1 Jun. 4, 2015

Related U.S. Application Data

(60) Provisional application No. 61/654,697, filed on Jun. 1, 2012.

(51) Int. Cl.
*H04N 7/18* (2006.01)
*H04N 13/00* (2018.01)
(Continued)

(52) U.S. Cl.
CPC ........... *H04N 7/18* (2013.01); *A61B 1/00009* (2013.01); *A61B 1/00048* (2013.01);
(Continued)

(58) Field of Classification Search
CPC .. H04N 7/18; H04N 13/0011; H04N 13/0022; H04N 13/0239; H04N 13/0242;
(Continued)

(56) References Cited

U.S. PATENT DOCUMENTS 5,123,726 A 6/1992 Webster
5,124,797 A 6/1992 Williams et al.
(Continued)

FOREIGN PATENT DOCUMENTS

FR 2699296 A1 6/1994
GB 2329545 A 3/1999
(Continued)

OTHER PUBLICATIONS

Office Action for Japanese application 2013-542142 dated Aug. 17, 2015, 11 pages including English translation.
(Continued)

*Primary Examiner* — Thai Tran
*Assistant Examiner* — Christopher T Braniff
(74) *Attorney, Agent, or Firm* — Thorpe North & Western, LLP

(57) ABSTRACT

Systems and methods for viewing stereoscopic video images are disclosed. The systems can include a first video camera configured to generate a first video feed of a subject, and a second video camera configured to generate a second video feed of the subject. The first video feed and the second video feed combined generate a near real-time stereoscopic video image. A tracking module can be associated with the first video camera and the second video camera, and can be configured to cause the first video camera and the second video camera to be directed to a desired convergent point relative to a selected tracking point to maintain stereopsis. The system may further include an array of video cameras,
(Continued)

a gesture control module, an image adjustment module, a calibration module, or a 3-D modeling module, for example.

20 Claims, 10 Drawing Sheets

(51) Int. Cl.
  *G06F 3/01* (2006.01)
  *H04N 13/02* (2006.01)
  *A61B 1/00* (2006.01)
  *A61B 1/04* (2006.01)
  *A61B 1/24* (2006.01)

(52) U.S. Cl.
  CPC ...... *A61B 1/00188* (2013.01); *A61B 1/00193* (2013.01); *A61B 1/04* (2013.01); *A61B 1/24* (2013.01); *G06F 3/017* (2013.01); *H04N 13/0011* (2013.01); *H04N 13/0022* (2013.01); *H04N 13/0239* (2013.01); *H04N 13/0242* (2013.01); *H04N 13/0246* (2013.01); *H04N 13/0296* (2013.01); *H04N 13/0275* (2013.01); *H04N 2213/003* (2013.01)

(58) Field of Classification Search
  CPC ........... H04N 13/0246; H04N 13/0296; H04N 13/0275; A61B 1/00009; A61B 1/00048; A61B 1/00188; A61B 1/00193; A61B 1/04; A61B 1/24; G06F 3/017
  See application file for complete search history.

(56) References Cited

U.S. PATENT DOCUMENTS

| | | |
|---|---|---|
| 5,151,722 A | 9/1992 | Massof et al. |
| 5,539,422 A | 7/1996 | Heacock et al. |
| 5,543,816 A | 8/1996 | Heacock |
| 5,662,111 A | 9/1997 | Cosman |
| 5,774,096 A | 6/1998 | Usuki |
| 5,825,540 A | 10/1998 | Gold et al. |
| 5,848,967 A | 12/1998 | Cosman |
| 5,864,360 A | 1/1999 | Shigeki et al. |
| 5,898,520 A | 4/1999 | Curatu |
| 5,917,460 A | 6/1999 | Kodama |
| 5,961,456 A | 10/1999 | Gildenberg |
| 5,991,085 A | 11/1999 | Rallison |
| 6,006,126 A | 12/1999 | Cosman |
| 6,219,186 B1 | 4/2001 | Hebert |
| 6,275,725 B1 | 8/2001 | Cosman |
| 6,326,994 B1 | 12/2001 | Yoshimatsu |
| 6,351,661 B1 | 2/2002 | Cosman |
| 6,396,627 B1 | 5/2002 | Tachihara et al. |
| 6,405,072 B1 | 6/2002 | Cosman |
| 6,480,174 B1* | 11/2002 | Kaufmann .......... G02B 27/0172 345/7 |
| 6,675,040 B1 | 1/2004 | Cosman |
| 6,856,314 B2* | 2/2005 | Ng ..................... G06K 9/20 345/419 |
| 6,900,777 B1 | 5/2005 | Herbert et al. |
| 7,436,568 B1 | 10/2008 | Kuykendall, Jr. |
| 8,477,175 B2 | 7/2013 | Shaffer et al. |
| 8,564,641 B1* | 10/2013 | Levin ................. H04N 13/0246 345/420 |
| 8,939,894 B2 | 1/2015 | Morrissette et al. |
| 9,545,188 B2 | 1/2017 | Jessop |
| 2002/0075201 A1* | 6/2002 | Sauer ..................... A61B 34/20 345/7 |
| 2002/0080094 A1 | 6/2002 | Biocca et al. |
| 2003/0067536 A1 | 4/2003 | Boulanger et al. |
| 2003/0207227 A1 | 11/2003 | Abolfathi |
| 2004/0138556 A1 | 7/2004 | Cosman |
| 2004/0224279 A1 | 11/2004 | Siemons |
| 2004/0238732 A1* | 12/2004 | State .................... G02B 27/017 250/250 |
| 2005/0020910 A1 | 1/2005 | Quadling et al. |
| 2005/0248852 A1 | 11/2005 | Yamasaki |
| 2006/0082647 A1 | 4/2006 | Donomae et al. |
| 2007/0121203 A1* | 5/2007 | Riederer ................. G02B 21/22 359/377 |
| 2008/0228438 A1* | 9/2008 | Lin ........................ G06T 7/593 702/152 |
| 2008/0239080 A1 | 10/2008 | Moscato |
| 2009/0187389 A1 | 7/2009 | Dobbins |
| 2009/0213114 A1 | 8/2009 | Dobbins |
| 2009/0228841 A1* | 9/2009 | Hildreth ................. G06F 3/0304 715/863 |
| 2010/0013739 A1 | 1/2010 | Sako et al. |
| 2010/0225735 A1 | 9/2010 | Shaffer et al. |
| 2010/0231734 A1 | 9/2010 | Cai |
| 2010/0253917 A1 | 10/2010 | Gao |
| 2011/0050547 A1 | 3/2011 | Mukawa |
| 2011/0102549 A1 | 5/2011 | Takahashi |
| 2012/0019623 A1 | 1/2012 | Kokuwa et al. |
| 2012/0025975 A1 | 2/2012 | Richey et al. |
| 2012/0050476 A1 | 3/2012 | Kawaguchi et al. |
| 2012/0069143 A1 | 3/2012 | Chu |
| 2013/0042296 A1 | 2/2013 | Hastings et al. |
| 2013/0060146 A1 | 3/2013 | Yang |
| 2013/0201276 A1 | 8/2013 | Pradeep et al. |
| 2013/0250067 A1 | 9/2013 | Laxhuber |
| 2014/0152550 A1 | 6/2014 | Beall et al. |
| 2016/0191887 A1 | 6/2016 | Casas |

FOREIGN PATENT DOCUMENTS

| | | |
|---|---|---|
| JP | H07-023429 | 1/1995 |
| JP | 2000/163558 | 6/2000 |
| JP | 2002/142233 | 5/2002 |
| JP | 2002-232913 | 8/2002 |
| JP | 2005-051472 | 2/2005 |
| JP | 2007518540 A | 7/2007 |
| JP | 2011-104186 | 6/2011 |
| JP | 2012-015661 | 1/2012 |
| KR | 10-2009-0041843 A | 4/2009 |
| WO | WO 03/081831 | 10/2003 |
| WO | WO 2005/093687 | 10/2005 |
| WO | WO 2007/066249 A2 | 6/2007 |
| WO | WO 2007/111570 A2 | 10/2007 |
| WO | WO 2012/075155 A2 | 6/2012 |

OTHER PUBLICATIONS

Heacock et al.; "Viewing Ocular Tissues with A Stereoscopic Endoscope Coupled to a Head Mounted Display"; http://www.hitl.washington.edu/publications/heacock; 8 pages as accessed Feb. 12, 2010.

LLU School of Dentistry-News; "Mora Vison 3-D System given test-run at LLUSD" (Loma Linda University School of Dentistry); Newsletter, Apr. 20, 2009; 2 pages.

Ostrovsky; "EndoSite 3Di Digital Vision System;" Viking Systems Inc.; Mar. 22, 2005; Medgadget LLC; 3 pages.

PCT Application No. PCT/US2013/029042; Filing date Mar. 5, 2013; Ultradent Products, Inc.; International Search Report dated Jul. 26, 2013.

PCT Application No. PCT/US2014/067181; Filing date Nov. 24, 2014; Ultradent Products, Inc.; International Search Report dated Feb. 24, 2015.

* cited by examiner

STEREOSCOPIC VIDEO IMAGING

BACKGROUND

Significant technological advancements have been made in the practice of dentistry. These advancements have enabled better patient care as well decreased anxiety for patients when visiting a dentist.

Many techniques now used by dentists to provide advanced care involve the ability to see and focus on very small details in a patient's mouth. Glasses with magnification loops are often used by dentists to increase their ability to view fine details. The glasses can be expensive and heavy, becoming burdensome for a dentist to wear for long periods of time. In addition, the magnification loops can cause eye strain and tunnel vision, reducing a dentist's ability to see both the magnified area and the surrounding area simultaneously.

Additionally, to obtain a desired view of the areas within a patient's intraoral cavity, a dentist often has to lean forward and hunch. Such posture can cause long term health problems for a dentist. Dentists that do not take precautionary measures regarding their posture can have their careers cut short or limited by back pain and other associated back problems. In addition, these injuries can significantly affect a dentist's quality of life outside of the dental office.

BRIEF DESCRIPTION OF THE DRAWINGS

Features and advantages of the present disclosure will be apparent from the following detailed description, taken in conjunction with the accompanying drawings, which together illustrate, by way of example, features of the invention.

Figure 1A:
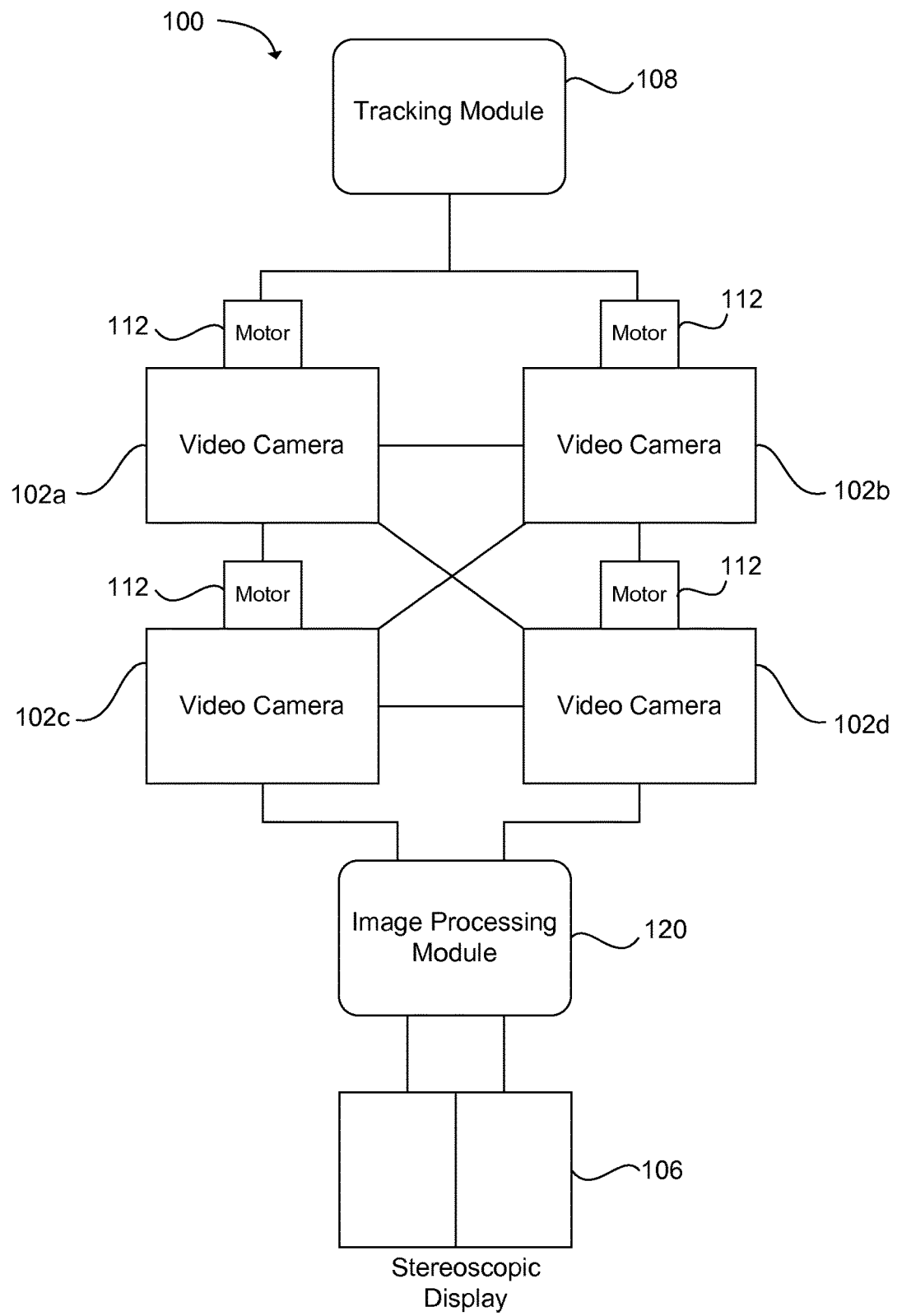
FIG. 1a illustrates a block diagram of a system for viewing stereoscopic video images using a pair of cameras selected from a plurality of at least three video cameras in accordance with embodiments of the present disclosure.
Figure 1B:
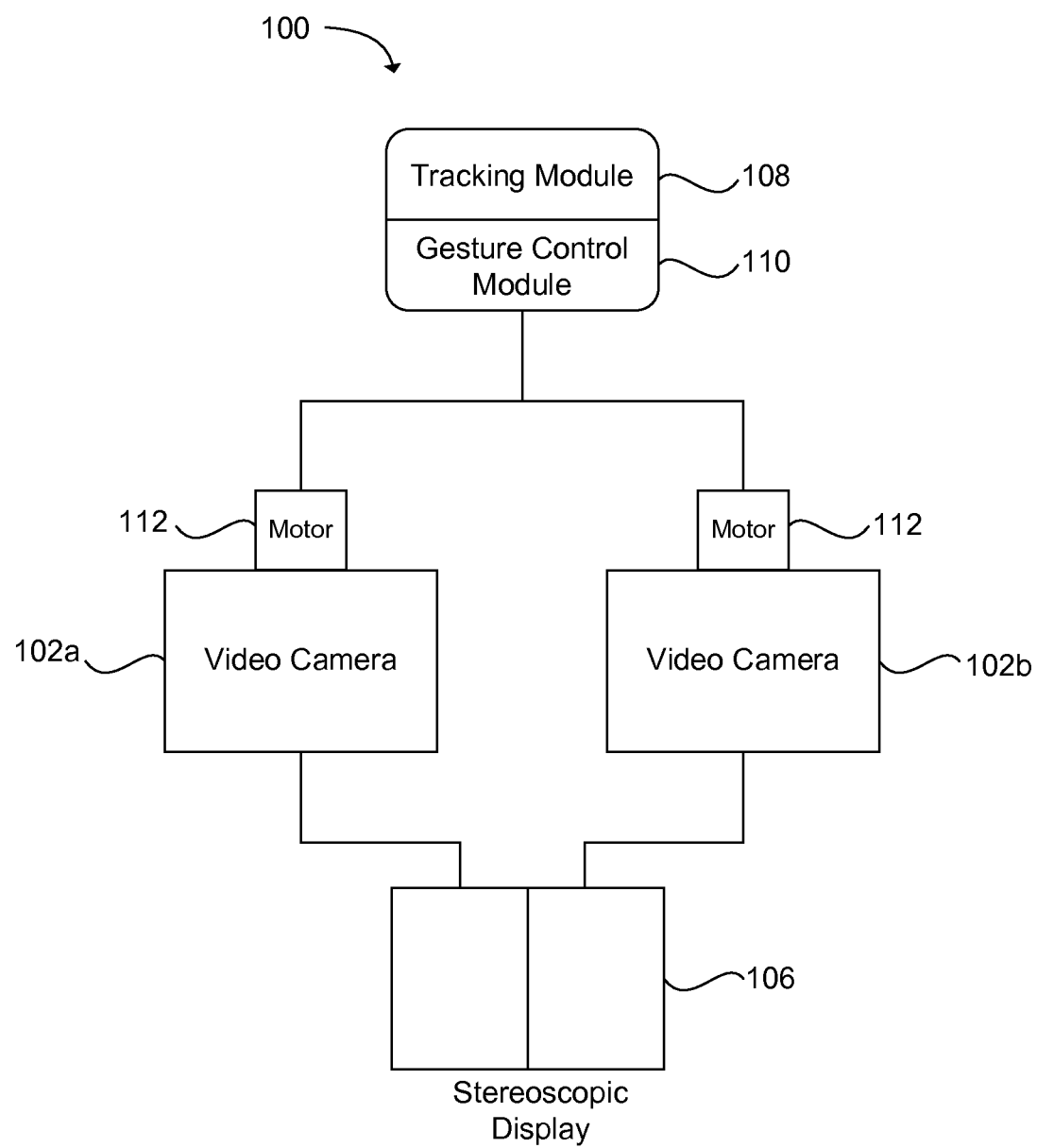
FIG. 1b illustrates a block diagram of a system for viewing stereoscopic video images using a gesture control module in accordance with embodiments of the present disclosure.

Reference will now be made to the illustrated exemplary embodiments, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

As a preliminary matter, it is noted that much discussion is related herein to the dental profession and conducting dental exams and procedures. However, this is done for exemplary purposes only, as the systems and methods described herein are also applicable to other medical professionals that would benefit from high magnification stereoscopic imaging and tracking of a desired site for surgery or examination. For example, the systems and methods herein can be especially useful in imaging locations where movement may occur, such as with minimally invasive surgeries when a patient is awake and moving or with examination of sites of interest of an alert patient. Additionally, the systems and methods of the present disclosure can also be applicable to viewing and tracking in the manner described herein that is outside of the medical professions generally, e.g., research, teaching, microbiology, electronics, jewel cutting, watch repair, etc.

With this in mind, an initial overview of technology embodiments is provided below and then specific technology embodiments are described in further detail thereafter. This initial description is intended to provide a basic understanding the technology, but is not intended to identify all features of the technology, nor is it intended to limit the scope of the claimed subject matter.

A dentist's ability to view a patient's intraoral cavity in detail is valuable for proper diagnosis of dental issues and performance of dental work in general. A magnified view of locations within the intraoral cavity can enable a dentist to adequately provide the advanced and complex solutions that are now available to patients. However, a typical solution to obtain a magnified view is through the use of glasses with one or more magnification loops. The use of magnification loops can strain a dentist's eyes and increase drowsiness. In addition, a dentist may need to lean forward and/or slouch in order to obtain a desired viewing angle inside of a patient's mouth. Over long periods of time, this can cause problems with posture, back pain, and debilitating physical damage to a dentist's back. Back pain and injury can reduce the length of the dentist's career and negatively affect the quality of his or her life outside of the dentist's office.

In accordance with embodiments of the present disclosure, systems and methods for viewing stereoscopic video images are disclosed. The systems and methods, in one example, enable a dentist to obtain a desired view of a patient's intraoral cavity while reducing eye strain and enabling the dentist to maintain a proper posture. It is noted that in other fields, such as medicine, electronics, teaching, microbiology, or any other field where high magnification stereoscopic vision may be useful, the systems and methods of the present disclosure are equally applicable. Thus, as mentioned discussion of dentistry is for exemplary purposes only and is not considered limiting except as specifically set forth in the claims.

That being said, in order to provide a desired level of care to patients, a hygienist, dentist, oral surgeon, or other type of dental professional should be able to delicately and accurately move dental tools in a desired direction. Typically, two dimensional images can make it challenging to accurately move dental equipment within a patient's intraoral cavity. The use of a stereoscopic image enables stereopsis to be maintained, thereby allowing a medical professional to perceive depth, enabling dental equipment to be accurately moved in a desired direction while viewing the stereoscopic image. As used herein, the term "stereopsis" refers to the process in visual perception leading to the sensation of depth from viewing two optically separated projections of the world projected onto a person's eyes, respectively. This can be through the use of a head mountable pair of video screens, each with a different optical projection, or though optical separation of the two optical projections on a single video screen, as will be described hereinafter in greater detail.

In addition, the systems and methods disclosed herein enable multiple persons viewing the stereoscopic video image to view a selected area from the same perspective. For instance, a dentist and a dental assistant can each view the same stereoscopic video image of a location such as a tooth or an area around a tooth in a patient's mouth. The capability for both the dentist and the dental assistant to view a stereoscopic video image of the area from the same perspective can significantly enhance the ability of the dental assistant to assist the dentist as needed. Moreover, the image may also be viewed by additional persons such as the patient or dental school students. The ability of the patient to view the same image as the dentist can enable the dentist to better educate the patient as to the condition of his or her teeth, and the procedures that will be conducted. Viewing the stereoscopic image can significantly enhance student's ability to learn and understand the teachings of their instructor from his or her viewpoint.

In accordance with one embodiment of the present disclosure, a system for viewing stereoscopic video images can comprise a plurality of video cameras including at least three spatially separated video cameras and a tracking module associated with the plurality of video cameras. The plurality of video cameras can be adapted so that multiple pairs of video cameras are capable of generating a near real-time stereoscopic video image, each of the multiple pairs comprising a first video camera configured to generate a first video feed of the subject and a second video camera configured to generate a second video feed of the subject. The tracking module can be configured to cause the first video camera and the second video camera to be directed to a desired convergent point relative to a selected tracking point to maintain stereopsis.

In another example, a system for viewing stereoscopic video images can comprise an array of video cameras configured for providing video camera feeds. An image processing module can be configured to i) receive video camera feeds from the array, ii) geometrically transform one or more of the video camera feeds to create a virtual camera feed; and iii) generate a stereoscopic video image from at least two camera feeds. In this example, at least one of the two camera feeds can be the virtual camera feed, and the at least two camera feeds can be directed to a convergent point. The system also includes a tracking module associated with the array, and the tracking module can be configured to follow a tracking point relative to the convergent point in order to maintain stereopsis.

In other examples, systems for viewing stereoscopic video images can comprise a first video camera configured to generate a first video feed of a subject and a second video camera configured to generate a second video feed of the subject, wherein the first video feed and the second video feed combine to generate a near real-time stereoscopic video image. These systems can further comprise a tracking module associated with the first video camera and the second video camera. The tracking module can be configured to cause the first video camera and the second video camera to be directed to a desired convergent point relative to a selected tracking point to maintain stereopsis.

In one specific example, a gesture control module can be associated with the system, wherein the system responds based on movement of a user. The gesture control module can include a sensor that senses movement of the user, for example. In another independent example, an image adjustment module can be configured to selectively modify an image received by the first video camera and the second video camera, thereby providing a viewable image having at least one adjusted visual property adapted for enhanced diagnostic or treatment visualization. In yet another specific example, a calibration module can be configured to calibrate and adjust horizontal alignment of the first video feed and the second video feed. In still another independent example, a 3-D modeling module can be configured to convert the stereoscopic video image into a 3-D model or construct.

Turning now to the FIGS., various embodiments of systems 100 for viewing stereoscopic video images are disclosed, as provided in further detail in the example illustrations of FIGS. 1 a-h. There are several commonalities between each of these embodiments, including the tracking module 108, the first video camera 102a, the second video camera 102b, motors 112, and the stereoscopic display 106. Other modules or camera configurations are described in more specific detail with respect to certain embodiments of the present disclosure. Thus, some features will be discussed generally with respect to FIGS. 1a-h, and others will be discussed specifically with respect to a particular FIG. That being stated, any combination of features described herein can be practiced in accordance with examples of the present disclosure.

With specific reference to FIG. 1a, the system 100 comprises a plurality of video cameras 102a-d that are spatially separated from one another. The plurality of video cameras can be adapted so that multiple pairs of video cameras are capable of generating a near real-time stereoscopic video image, each of the multiple pairs can comprise a first video camera configured to generate a first video feed of a subject and a second video camera configured to generate a second video feed of the subject. For example, video camera 102a and 102b can be the first video camera and the second video camera in one situation, and video cameras 102c and 102d can be the first and second video cameras in a second situation. Furthermore, the video cameras need not be discrete pairs that are always used together. For example, video camera 102a and video camera 102c or 102d can make up a third pair of cameras, and so forth. Regardless of which two cameras are selected for use, in a dental environment, for example, the first video camera can be directed toward the subject to create a first video feed of a patient's intraoral cavity, and a second video camera can be spaced appropriately at a selected distance from the first video camera to create stereopsis. It is noted that the multiple pairs of video cameras can be spatially separated at a pupillary distance from one another, or can be positioned so that they are not necessarily a pupillary distance from one another, e.g., at a simulated pupillary distance with appropriate angles that are optically aligned with the pupillary distance, or spaced out of optical alignment with the pupillary distance with some signal correction being typical.

The plurality of video cameras can be positioned in a one-dimensional array, such as in a straight line, e.g., 3, 4, 5, . . . 25 video cameras, etc., or an a two-dimensional array, e.g., in an arrangement configured along an x- and y-axis, e.g., 3×3, 5×5, 4×5, 10×10, 20×20 cameras, and so forth. Thus, in either embodiment, any two adjacent video cameras can be used as the first video camera and the second video camera. Alternatively, any two video cameras that may not be adjacent to one another might also be used to provide the stereoscopic image. Selection of which two video cameras to use can be based on manual selection (such as by positive gesture control, or selection of appropriate buttons, switches, or other interface controls), or can be automatic based on movement of a user, e.g., a dental professional, or a subject, e.g., patient.

In another related example regarding the array of cameras, any of the multiple cameras 102a-d (or typically many more video cameras arranged in an array) can likewise be used to generate a virtual perspective that can arise from the placement of a static array of cameras in a particular orientation in the Cartesian space. For example, the various video cameras can be positioned so that they are known relative to one other and relative to a user or subject of the system. The position of the user or subject within the system can also be known via tracking methods described herein, or as otherwise known in the art, via hardware (e.g., Polhemus' magnetic tracking or other tracking systems or modules) or via software.

In such a system, camera feeds are taken into an image processing module 120 and geometrical transformations can be performed on one or more camera feeds to create virtual camera feeds that present new perspectives, i.e. perspectives other than those generated directly from the camera feeds per se. These virtual camera feeds are then multiplexed to a stereoscopic or 3-D signal for a stereoscopic display or sent to a head mounted display (e.g., right eye, left eye), to create a stereoscopic video. Hardware and software packages, including some state of the art packages, can be used or modified for this purpose. For example, NVIDIA has a video pipeline that allows users to take in multiple camera feeds, perform mathematical operations on them, and then output video feeds that have been transformed geometrically to create virtual perspectives that are an interpolation of actual video feeds. These video signals are typically in the Serial Digital Interface (SDI) format. Likewise, software used to perform such transformations is available as open source. OpenCV, OpenGL and CUDA, which can be used to manipulate the video feed. In order to create stereopsis, the images designed for the left and right eye or optically separated video feed to a single screen, whether virtual or real images are displayed, are typically separated by a pupillary distance or simulated pupillary distance, though this is not required. It is noted that the image processing module shown in this example for purposes of generating virtual camera feeds. However, any other type of image processing that may be beneficial for use in this embodiment or any other embodiment herein that would benefit from image processing can also include an image processing module.

In either of these two embodiments, i.e. pairing of various video cameras from a plurality of camera feeds or generating a virtual image using an array of cameras, there are many ways of controlling the selection of video cameras or generation of virtual images. User or subject movement, for example, may be used to control these systems, and may include movement of a user's head or eyes, or movement of a subject's intraoral cavity. The automatic selection can be configured to provide a desired image based on a position of the dental professional or patient relative to one another. For instance, when the dental professional changes the angle at which he or she is viewing the patient, cameras in the array can be selected and/or moved to provide an image based on the viewing angle of the dental professional.

In further detail regarding gesture controls, FIG. 1 b sets for a gesture control module 110 that is associated with the systems 100 of the present disclosure. Though some details regarding gesture controls were described previously with respect to selection of a pair of cameras from a plurality of at least three video cameras, gesture controls are also applicable to embodiments where only two video cameras are present as well. More specifically, the gesture control module can include a sensor that senses movement of a user, such as a dental professional, and responds based on that movement. Gestures can either be deliberate to cause an action, or can be incidental to typical movements of the user. A deliberate gesture might include hand or arm gesture, or deliberate movement of an instrument held in the hand of the user. A voice gesture, e.g., voice commands, is also an example of a deliberate gesture.

Alternatively, the system of the present disclosure can also controlled by incidental movements by the user, such as causing the tracking module to follow a tracking point based on eye or head movement of the user. When tracking eye movement, sensors can be directed to or present near the user's eyes, such as a camera directed to the user's eyes or sensors on a pair of glasses used to optically separate a stereoscopic image on a video screen or on head mountable stereoscopic display. Thus, the camera or sensors can be used to detect a movement of the user's eyes, and/or the cameras in the array can be selected and/or moved to provide an image based on the viewing angle of the user's (i.e. dental professional's) eyes. In either case, gestures can be used to move a tracking point, adjust light settings, modify a level of magnification (using a zoom module), or any other adjustment that may be desirable for use with the systems of the present disclosure.

Figure 1C:
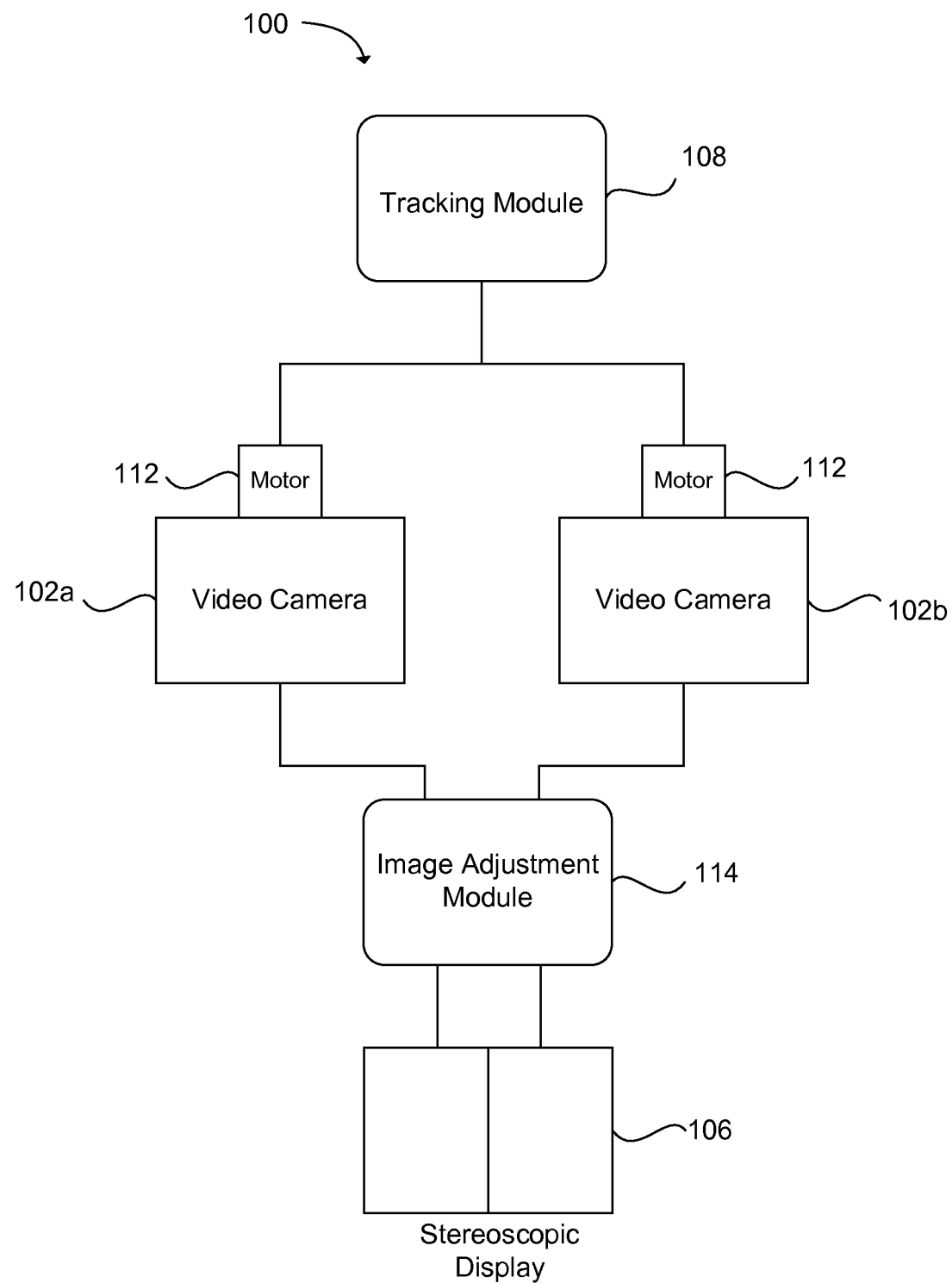
FIG. 1c illustrates a block diagram of a system for viewing stereoscopic video images having an image adjustment module in accordance with embodiments of the present disclosure.

Turning now to the system 100 of FIG. 1c, in addition to the tracking module 108, motor 112, first video camera 102a, second video camera 102b, and stereoscopic display 106 set forth in this embodiment, each of which will be described in further detail hereinafter, an image adjustment module 114 is also included. The image adjustment module can be configured to selectively modify images received by a first video camera and a second video camera and provide a viewable image having at least one adjusted visual property adapted for enhanced diagnostic or treatment visualization.

For example, the adjusted visual property may include enhancement or shifting of a specific optical frequency band for enhanced resolving power of a dental professional to view the specific optical frequency band. Specifically, a color or group of colors can be enhanced or shifted in viewable color, such as for diagnosing or treating cancers or lesions in the mouth, diagnosing or treating soft tissue anomalies (e.g., gums, tongue, cheek, etc.), diagnosing or treating teeth (e.g., cavities), etc. To provide a more specific example infrared, green, amber, white, violet, ultraviolet, or a combination of these light frequencies can be used to enhance the detection of cancerous tissue. The image detected by the cameras can be so modified such that the coloration is enhanced using the image adjustment module for diagnosis or treatment purposes.

In another example, there are circumstances where specific lighting profiles are used (or avoided) in conjunction with some materials, e.g., amber light or UV light. For instance, UV lighting may be used to cure certain materials. Amber lighting may be used when curing of materials is not desired. Thus, the system can be adapted for use under that specific lighting profile, and the adjusted visible property can be to decrease the artificial coloration of the viewable image on the stereoscopic display, making it appear more natural to the user, e.g., amber light environment where the amber light is minimized and other light is enhanced that may be only minimally present.

In still another example, the system can be adapted for use in highly saturating light, and the adjusted visible property can be to decrease the white or other saturation of the viewable image. This may be useful when there is a desire to more accurately visualize a certain color, such as when matching off-white coloration for cosmetic or reconstructive dentistry. In yet another example, there may be advantages in utilizing the system to detect and shift otherwise invisible light into the visible spectrum, e.g., ultraviolet light such as 405 nm light. If this is the case, sensors on the video cameras, such as charged couple device (CCD) sensors or complementary metal oxide semiconductor (CMOS) sensors can be selected that are sensitive to ultraviolet light. In one embodiment, multiple sensors may be provided in a single camera, with different sensors tuned to different parts of the light spectrum. For instance, one sensor may be configured to detect wavelengths from infrared to blue, while another sensor may be configured to detect ultraviolet wavelengths. The appropriate sensor in each camera can be selected based on the color (i.e. wavelength) of light being imaged by the cameras.

In related embodiments, the adjusted visual property can be further enhanced by the presence of a colorant. By selecting certain colorants (pigments or dyes) for use in the intraoral cavity, certain materials or conditions can be amplified. This, coupled with the ability to adjust a visual property of the colorant can provide a combination that would make certain dental tasks easier for the dental professional to visualize. For example, a dye or pigment may be used, and the video image can be used to enhance or even shift coloration of the dye or pigment, making it more easily viewable. In one specific example, certain fluorescent dyes or pigments can be used for determining the presence of a dental material, such as a bonding cement, and the coloration can help the dental professional determine whether it is properly cured. In another example, a colorant can be used to attach to certain types of dental conditions, such as cavities, lesions, cancers, or the like, to assist the dentist in diagnosing or treating a dental condition. The digital imaging sensors in the cameras and/or the output signals of the digital imaging sensors can be configured to enhance the view of the colorant on the stereoscopic display 106.

Figure 1D:
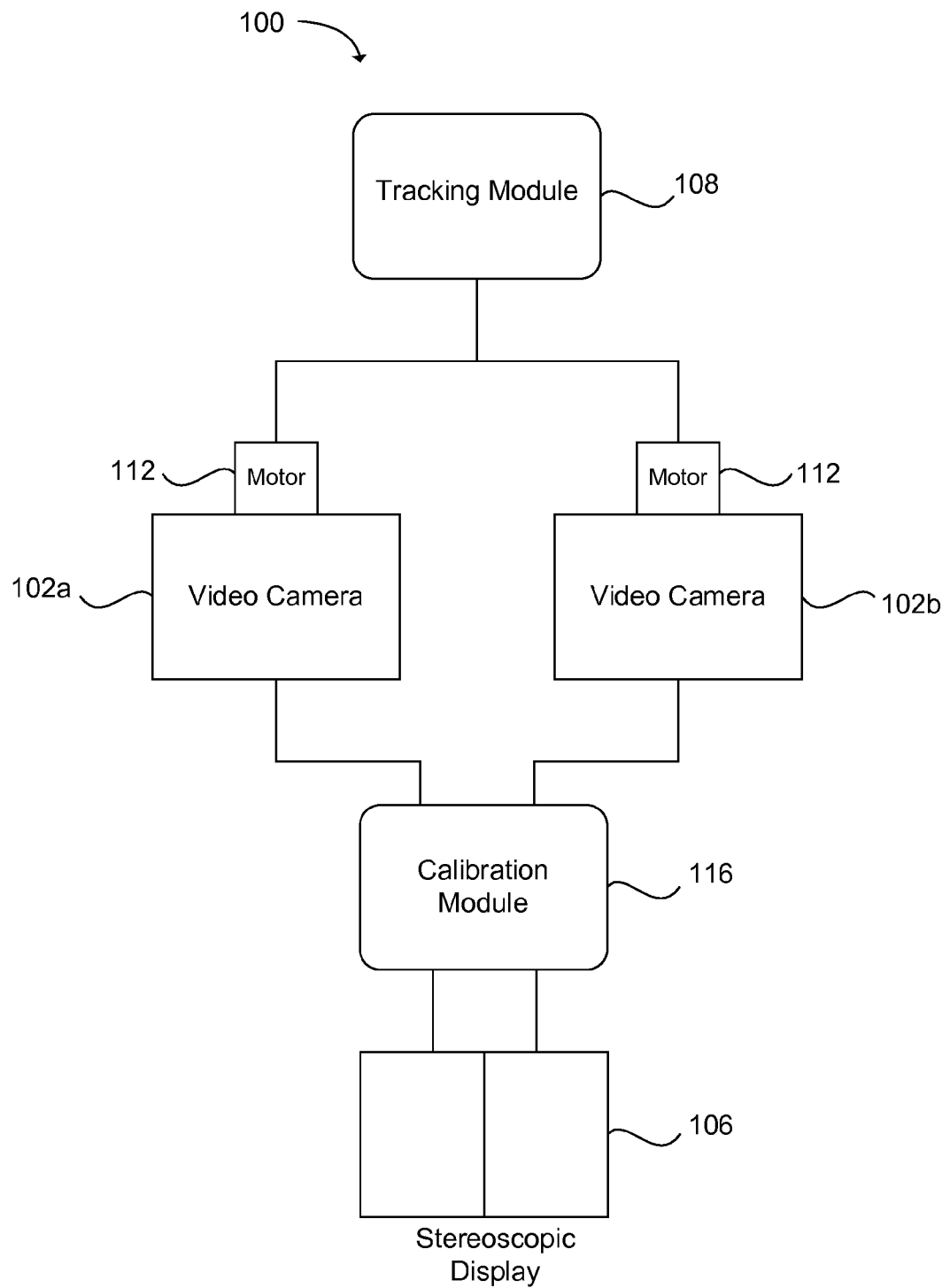
FIG. 1d illustrates a block diagram of a system for viewing stereoscopic video images having a calibration module in accordance with embodiments of the present disclosure.

FIG. 1d sets forth a system 100 that includes a calibration module 116, in addition to the tracking module 108, motor 112, first video camera 102a, second video camera 102b, and stereoscopic display 106. The calibration module can be configured to calibrate and adjust horizontal alignment of a first video feed and a second video feed so that the pixels from the first video camera are aligned with the pixels of the second video camera. When the stereoscopic display is a head mountable stereoscopic display including a right video display and a left video display, proper alignment of the two images can be calibrated to the eyes of the user horizontally so that the image appears as natural as possible. The more unnatural an image appears, the more eye strain that can result. Horizontal alignment can also provide a clearer image when viewing the near real-time stereoscopic video image on a screen (with or without the assistance of viewing glasses). When the pixels are properly aligned, the image appears more natural and sharper than might be the case when the pixels are misaligned even slightly. Additional calibration can also be used to adjust the vertical alignment of the first video camera and the second video camera to a desired angle to provide stereopsis. In either case, whether the calibration module is used to for vertical or horizontal alignment, the alignment can be configured to be maintained or recalibrated when something changes, e.g., after pan or tilt movements of the first video camera or the second video camera, the selection of different video cameras to pair in the array, and so forth. These movements may cause minor misalignment that can be readjusted as the misalignment occurs. The calibration module can be configured to allow manual adjustment and/or automatic adjustment of horizontal and/or vertical alignment of the camera pair.

Other uses for calibration can occur when the system is first set up, or when multiple users are using the same equipment. In one example, the calibration module can provide for calibration with multiple users. Thus, the system can be calibrated for a first user in a first mode and a second user in a second mode, and so forth. For example, a focus of each camera in the camera pair can be adjusted to compensate for vision differences. The system can be configured to switch between the first mode and the second mode automatically or manually based on whether the first user or the second user is using the system.

Figure 1E:
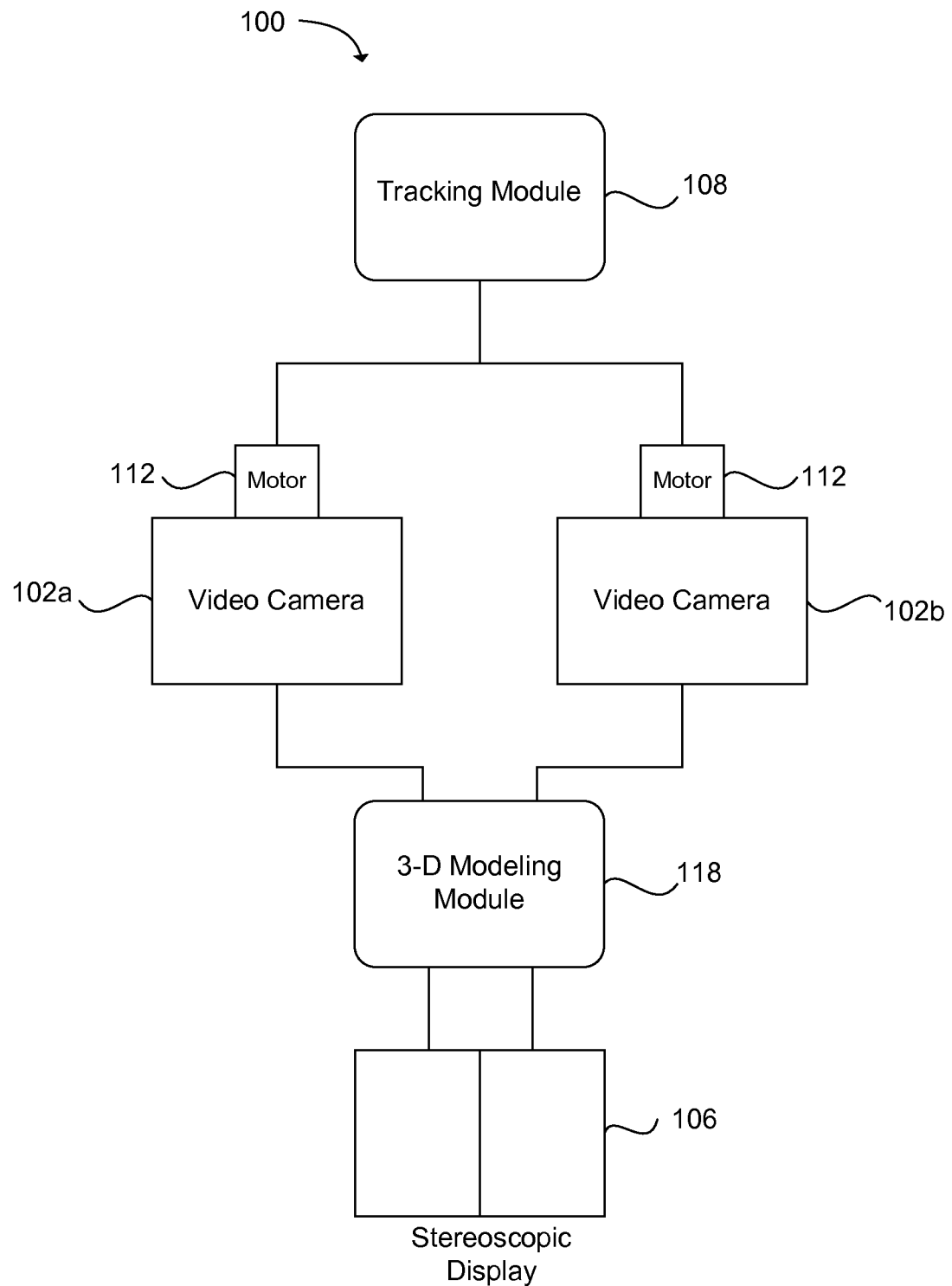
FIG. 1e illustrates a block diagram of a system for viewing stereoscopic video images having a 3-D modeling module in accordance with embodiments of the present disclosure.

FIG. 1e sets forth a system 100 that includes a 3-D modeling module 118, in addition to the tracking module 108, motor 112, first video camera 102a, second video camera 102b, and stereoscopic display 106. The 3-D modeling module can be configured to convert the stereoscopic video image into a 3-D model or construct. This module can output one or more frame of the stereoscopic video image to a modeling device, such as a 3-D printer, tooth impression modeling device, or a 3-D CAD drawing that can be further used to prepare a 3-D model. Any 3-D modeling technique can be used, as is known in the art, once the stereoscopic image is outputted to the appropriate technology for generating a 3-D model or construct.

Figure 1F:
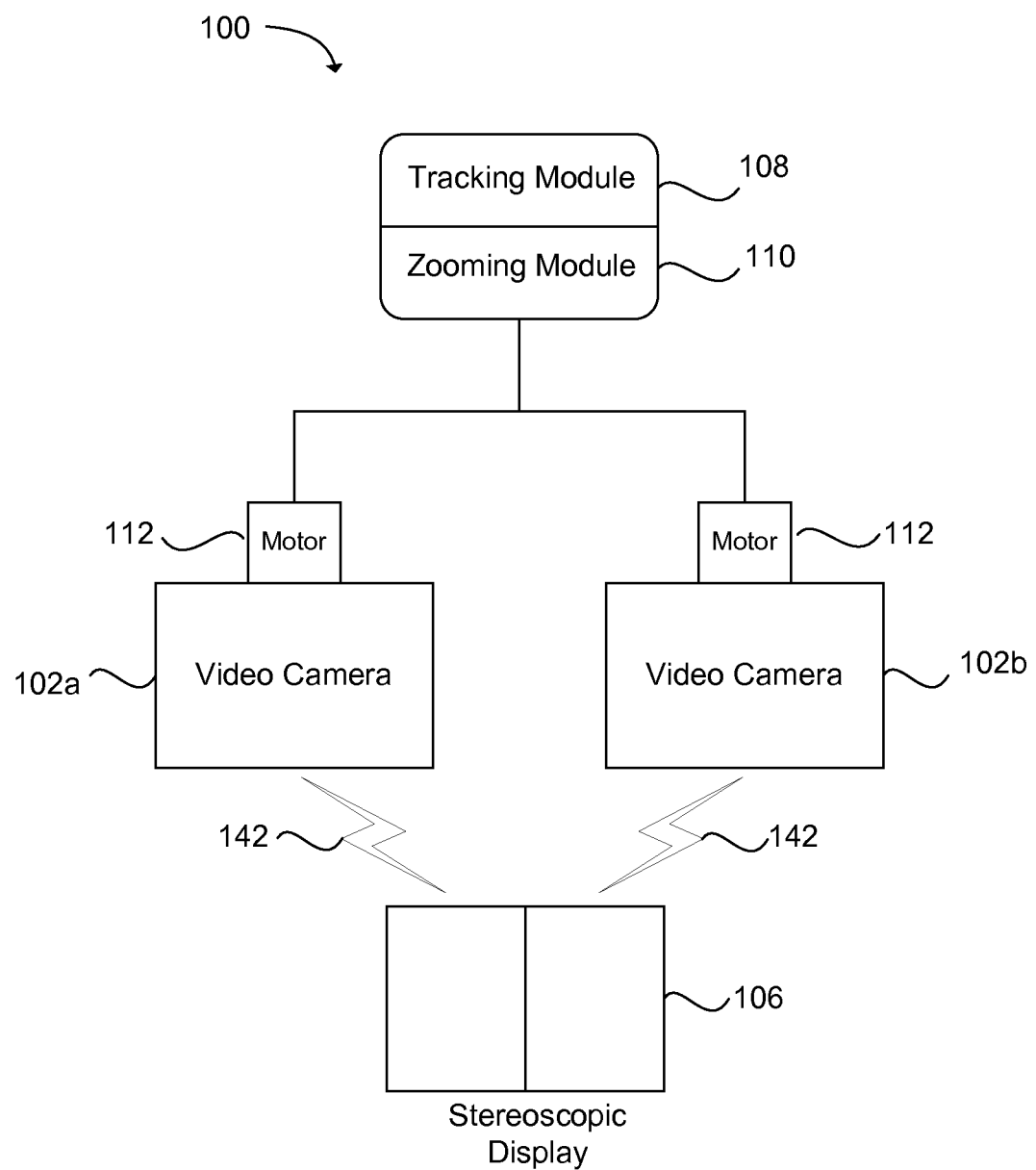
FIG. 1f illustrates a block diagram of a system for viewing stereoscopic video images with a wireless data link in accordance with embodiments of the present disclosure.
Figure 1G:
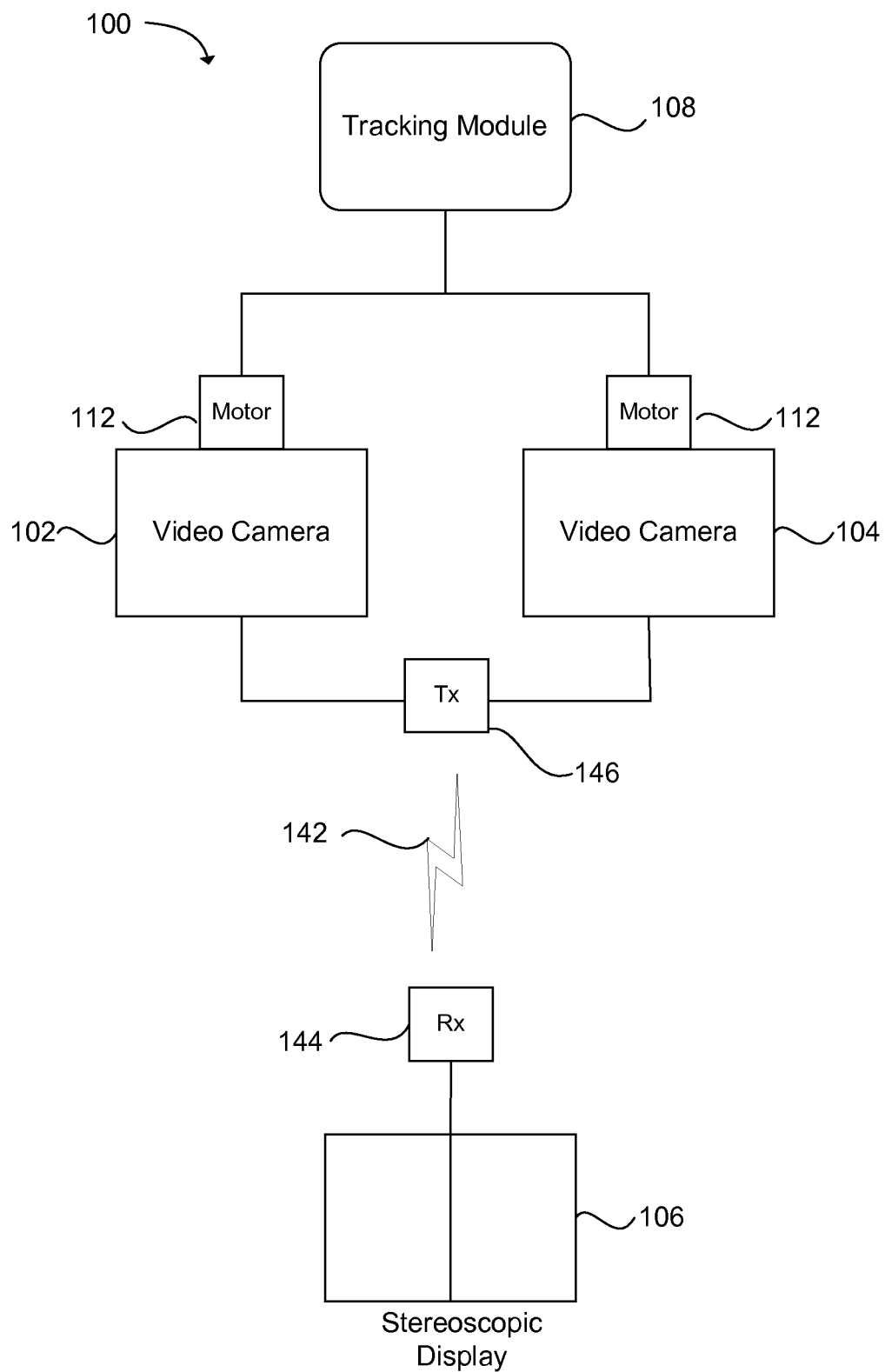
FIG. 1g illustrates a block diagram of a system for viewing stereoscopic video images with a wireless data link comprising a single transmitter and receiver in accordance with embodiments of the present disclosure.

In the embodiments described above in FIGS. 1a-e, the first video feed from the first video camera 102a and the second video feed from the second video camera 102b can be communicated to the stereoscopic video display 106 through wired communication cables, such as a digital visual interface (DVI) cable, a high-definition multimedia interface (HDMI) cable, component cables, and so forth. Alternatively, the information from the first video feed and the second video feed can be communicated wirelessly to the stereoscopic video display. For instance, FIG. 1f shows a system 100 that provides a wireless 142 data link between the video display and each of the first video camera and the second video camera. In yet another example, as displayed in FIG. 1 g, the first and second video feeds are communicated via a wired connection to a single transmitter 146. The transmitter can wirelessly 142 communicate the first and second video feeds from the first and second video cameras, respectively, to the video display. A wireless receiver 144 at the video display can be used to receive the first and second video feeds from the transmitter and communicate the video feeds to the video display.

Various standards which have been developed or are currently being developed to wirelessly communicate video feeds include the WirelessHD standard, the Wireless Gigabit Alliance (WiGig), the Wireless Home Digital Interface (WHDI), the Institute of Electronics and Electrical Engineers (IEEE) 802.15 standard, and the standards developed using ultrawideband (UWB) communication protocols. In another example, the IEEE 802.11 standard may be used to transmit the signal(s) from the video cameras 102, 104 to the stereoscopic display 106. One or more wireless standards that enable the video feed information from the first and second video feeds to be transmitted to the stereoscopic video display for display in near-real time can be used to eliminate the use of wires and free the user to move about more freely. This can be especially useful when the stereoscopic video display is head mountable, though it is also desirable in any of the video display embodiments described herein.

Figure 1H:
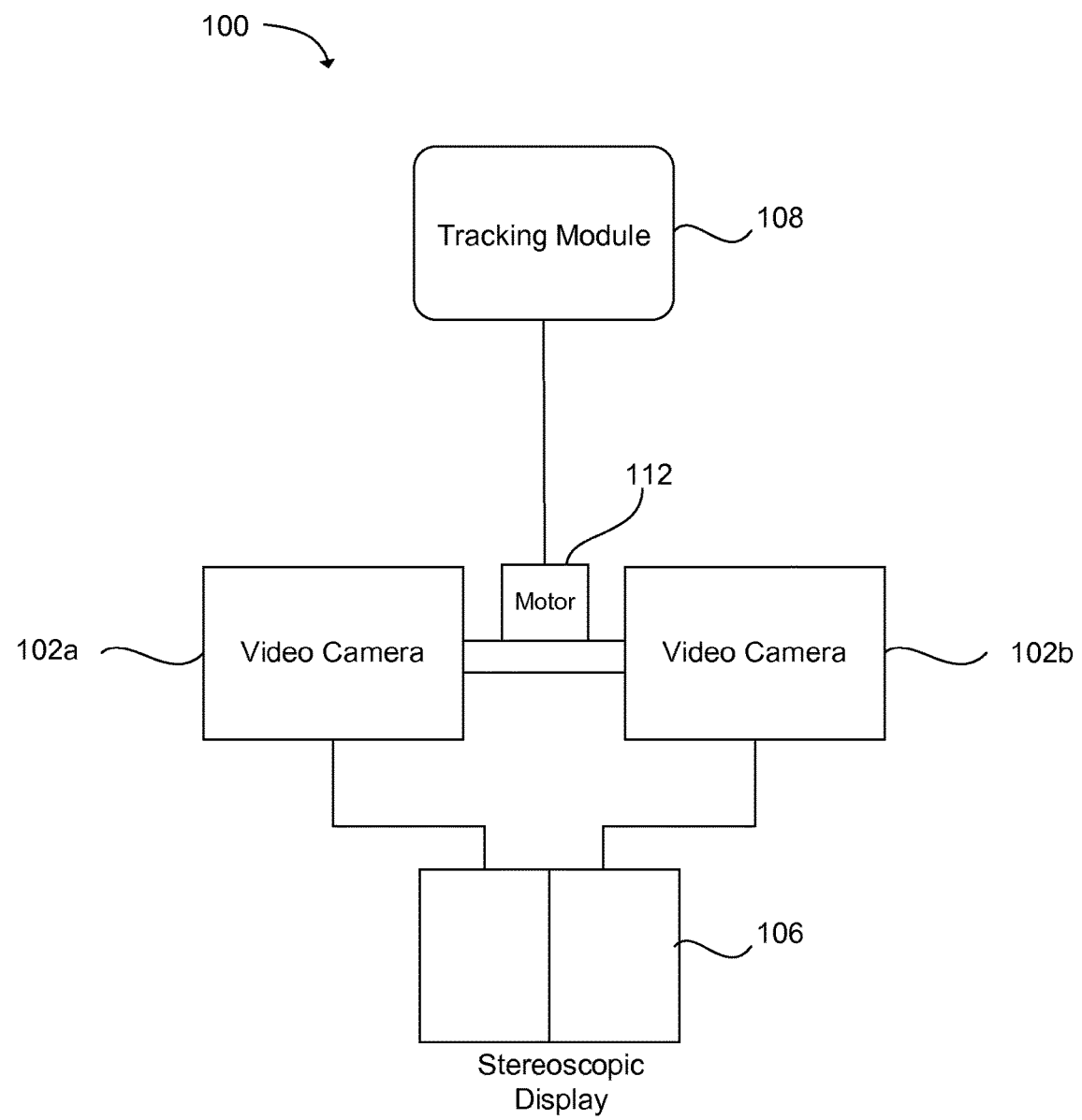
FIG. 1h illustrates a block diagram of a system for viewing stereoscopic video images with a single motor used to update a position of first and second video cameras in accordance with embodiments of the present disclosure.

In further detail with respect to FIGS. 1a-g, it is noted that each camera that is shown can include an individual motor associated therewith to control a direction and/or focus of the camera. FIG. 1h provides an example illustration of another embodiment, wherein a single motor 112 is used to update a position of the first and second video cameras 102a, 102b together. The single motor can be mechanically coupled to the first and second video cameras. For example, the motor may be connected through a series of gears and/or screws that allow the motor to be used to change an angle in which the video cameras are directed. Other types of mechanical couplings can also be used, as can be appreciated. Any type of mechanical coupling that enables the motor to update a direction in which one or both of the first and second video cameras are pointed is considered to be within the scope of this embodiment.

In each of the embodiments described in FIGS. 1a-h, as mentioned, there are several details regarding various elements of the FIGS. that have some commonality. Some of these features will be discussed together hereinafter. For example, regarding the spacing of the first video camera 102a and the second video camera 102b, the cameras can be horizontally spaced to simulate the spacing between a person's eyes in order to produce a first video feed and a second video feed that is combinable to generate a natural stereoscopic image, e.g., the image can be displayed to simulate a person's vision from his or her left eye and right eye. This spacing can be referred to as pupillary distance. A typical pupillary distance is from about 50 millimeters (mm) to about 75 mm. Alternatively, the cameras may be spaced a different (typically greater) distance apart, but can still be optically or digitally aligned to provide approximately the pupillary distance. In other embodiments where the distance between the cameras is not the pupillary distance or at least does not optically simulate the pupillary distance, some signal processing may be desirable to otherwise compensate for more unnatural camera convergence angles and distances therebetween.

The systems can further comprise a stereoscopic video display 106, as shown in FIGS. 1 a-h. In one embodiment, the stereoscopic display can be a head mountable stereoscopic display with a right video display viewable by a person's right eye and a left video display viewable by a person's left eye. By displaying the first and second video feeds in the left and right video displays, a near real-time stereoscopic video image can be created. Alternatively, the stereoscopic display can be a single video screen wherein the first video feed and the second video feed are optically separated, e.g., shutter separation, polarization separation, color separation, etc. The stereoscopic display can be configured to allow a user to view the stereoscopic image with or without an external viewing device such as glasses. In one embodiment, a pair of appropriate glasses that work with shutter separation, polarization separation, color separation, or the like, can be used to allow the screen to be viewed in three-dimensions. Still further, the video display can comprise multiple video displays for multiple users to view the near real-time stereoscopic video image, such as the dental assistant and/or the patient.

The stereoscopic video image provides a visual perception leading to the sensation of depth from the two slightly different video images projected onto the retinas of the person's two eyes. This visual perception leading to the sensation of depth is referred to as stereopsis. No additional video or computer processing of the first and second video images may be needed when using the head mountable stereoscopic display or the other optical separation technology described above. The sensation of depth is created due to the differing projections of the first and second cameras that are separated by, for example, a pupillary distance or simulated pupillary distance. That being stated, there are instances where the cameras may be further apart or angled in a manner that does not correspond to a typical pupillary distance, and in those arrangements, the near real-time stereoscopic video image can thus be corrected to provide a simulated pupillary distance based on the images received from two or more cameras in the camera array, as previously discussed.

The ability to perceive depth can be valuable to a dentist that is working with a patient. Proper depth perception enables the dentist to make small, but critical movements when performing dentistry. Previously, the lack of ability to display depth perception has limited the use of cameras and display screens in the practice of dentistry. With the use of two separate cameras that are configured to provide a display with stereopsis, a dentist can view the resulting stereoscopic display that provides the sensation of depth, thereby enabling the dentist to maintain substantially the same hand-eye coordination that the dentist has learned during his or her practice using loops or other magnification systems.

Returning to FIGS. 1a-h, the various systems 100 can also include a tracking module 108 that is in communication with the first video camera 102a and the second video camera 102b (or the plurality of video cameras as described specifically in FIG. 1a). The tracking module can be configured to cause the first video camera and the second video camera to be directed to a desired convergent point relative to a selected tracking point.

The tracking point can be a selected location on or about the patient's body that enables the cameras 102a, 102b to be redirected relative to the motion of the tracking point. For instance, the tracking point may be at a location on the patient's head. When the patient moves his or her head, the cameras can move with the patient so that the image on the display screen is not substantially changed due to movements of the patient. Alternatively, the tracking point may be located at or about a dental patient's intraoral cavity. For instance, the tracking point may be located on a tooth, a dental tool, or on a dental retractor located in or about the patient's intraoral cavity. Further, as discussed with respect to certain examples herein, the tracking point can be associated with the user, e.g., the dental professional, and movement of the user can relate directly to the tracking function.

The tracking point can be provided by any type of device, object, or signal that enables the movement of the patient to be tracked relative to the position of the cameras. For instance, tracking may be accomplished using radio frequency triangulation. Multiple tracking transceivers can be located on or about the patient. A marker, such as a tool, can also include a transceiver. The location of the tool relative to the location of the markers can be calculated based on the timing of the arrival of tracker signals transmitted from the tool transceiver at the tracking transceivers. The location of the tool transceiver can be calculated using trigonometry, for example.

In another embodiment, the tracking point may be an optically trackable marker such as a reflective dot or an optical dot formed using a different colored light or an infrared light source. The light sources for the colored light or the infrared light may be one or more light emitting diodes or lasers. The tracking module can include image recognition software that enables the cameras to be substantially directed relative to the optically trackable marker. Alternatively, an infrared receiver can be used to track a location of an infrared optical dot.

In another embodiment, the tracking module 108 can include image recognition software may be used that can recognize a location or feature, such as a person's nostrils, eyes, or other distinct characteristics. As the person's selected feature moves, the position of the camera can be adjusted to maintain the stereoscopic video image of a selected area within the person's intraoral cavity. The ability to adjust a direction of the video cameras relative to movement of the patient can enable the video cameras to provide a relatively high amount of magnification of a desired location within the intraoral cavity. The image recognition software can be programmed to recognize patterns. For example, software that includes facial recognition technology can be used with the systems of the present disclosure that is similar to that wide used with state of the art point and shoot digital cameras, e.g., boxes in digital display screens appear around faces to inform the user that a face of a subject has been recognized for focus or other purpose.

Accordingly, the systems of the present disclosure can also include an optional zooming module 110, shown in FIG. 1f. Though the zooming module is shown only in FIG. 1f, it is understood that the zooming module can be used in any of the embodiments described herein. The zooming module can be in communication with the first video camera 102a and the second video camera 102b. The zooming module can be configured to provide a desired magnification of the near real-time stereoscopic video image. As previously discussed, the ability to view a desired location with a selected magnification provides a significant advantage to a dentist to conduct complex and detailed procedures. Dentists typically use glasses with magnification loops to magnify images in the order of about 4 times. However, in accordance with embodiments of the present disclosure, zooming ranges are only limited by the zooming range of the first and second video camera.

In one specific embodiment, the video cameras 102a, 102b can be configured to provide a magnification from one time to over 20 times a standard image, or more. The magnification may be achieved either through the use of an optical magnification, a digital zoom, or a combination of the two. The stereoscopic display can provide a clear, focused image of the desired location within the patient's intraoral cavity at a high magnification. The video cameras can be set at substantially the same magnification to enable the visual perception leading to a sensation of depth to be maintained. In addition, the rate at which the cameras change magnification can be substantially the same to maintain stereopsis of the stereoscopic video image as the image is zoomed in and out using the zooming module to communicate with the first and second video cameras.

In another embodiment, the first and second video cameras 102a, 102b and the stereoscopic display 106 can be configured to display a relatively high resolution. For instance, the cameras and display can be configured to provide a 720P progressive video display with 1280 by 720 pixels (width by height), a 1080i interlaced video display with 1920×1080 pixels, or a 1080p progressive video display with 1920×1080 pixels. As processing power and digital memory continue to exponentially increase in accordance with Moore's Law, the cameras and display may provide an even higher resolution, such as 4320P progressive video display with 7680×4320 pixels. With higher resolution, an image can be magnified using software (digital zoom) to provide a digital magnification without substantially reducing the image quality. Thus, software alone may be used to provide a desired magnification level of the real-time stereoscopic video image.

Figure 2:
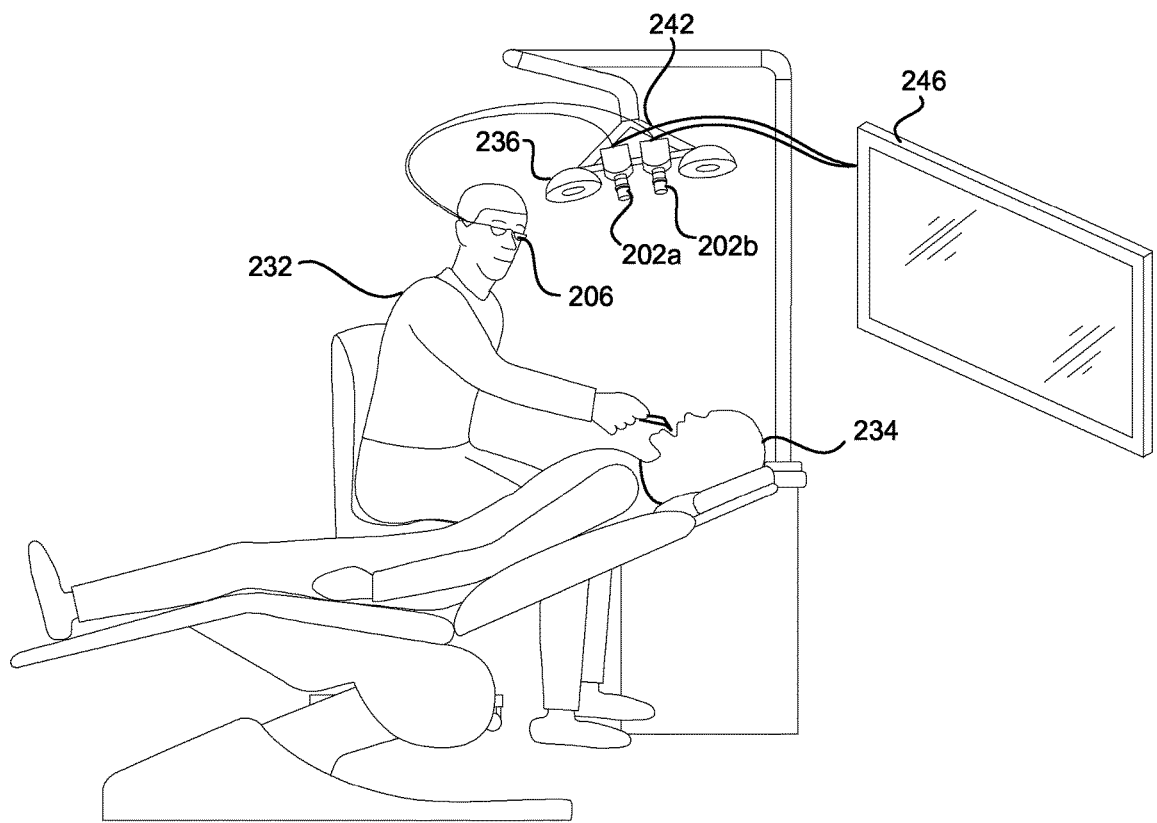
FIG. 2 provides an example illustration of a dental professional using a stereoscopic display to view a near real-time stereoscopic video image of a patient's intraoral cavity in accordance with embodiments of the present disclosure.

FIG. 2 provides an example illustration of a dentist 232 using a head mountable stereoscopic display 206 to view a near real-time stereoscopic image of a patient's intraoral cavity in accordance with one embodiment of the present disclosure. The first video camera 202a and the second video camera 202b can be mounted on a fixture 242 above the patient 234.

A light 236, such as a dental light source, can be provided to illuminate the patient's intraoral cavity. The light can provide sufficient illumination to enable the first video camera 202 and the second video camera 204 to zoom to a desired magnification level while maintaining a selected depth of field for the near real-time stereoscopic video image. The depth of field can be selected to enable the dentist to have a clear, focused view of all of the desired locations within the patient's intraoral cavity. The aperture of the first and second video cameras may change when the magnification provided by the video cameras is increased. Alternatively, the light source may be sufficiently bright that no change in aperture is needed. The light may also be provided to generate various lighting profiles that would be useful with the image adjustment module previously described in relation to FIG. 1c.

The depth of field of the first and second video cameras 202a, 202b may be greater than a length of the patient's intraoral cavity. For example, if the depth of field of the first and second video cameras is twice the depth of a typical patient's intraoral cavity, then the first and second video cameras can be focused on the patient's lip while maintaining a clear focus to the back of the patient's mouth, assuming that the depth of field of the cameras is centered.

In one embodiment, the head mountable stereoscopic video display 206 can be configured to provide a split field of view, with a bottom portion of the glasses providing separate high definition displays for the left and right eyes, and above the glasses, the dentist can view the environment unencumbered. Alternatively, the glasses can be configured in a split view where the bottom half provides the video image, and the top half of the glasses is substantially transparent to enable an operator to view both natural surroundings while wearing the head mountable stereoscopic display. This can be especially useful as the dentist is using a high magnification level while working on the patient's mouth and can move quickly to no magnification when viewing the surrounding environment.

Alternatively, a video display other than the head mountable stereoscopic video display can be positioned to display the near real-time stereoscopic video image as well. For instance, a large television screen can be configured to show three dimensional images. The placement is based on a desired application, but in one embodiment, it may be placed behind the patient 234 in a position that enables the dentist 232 to view the video image. It can also be placed for the patient to view, or for students to view for learning in an educational environment, for example. The video display can be configured to enable viewers to view the stereoscopic display 246 as a three dimensional image, either with or without the assistance of eyewear.

For instance, in one embodiment the first and second video feeds can be displayed on a single display screen 246, with the respective video feeds being optically separated. Technologies for optical separation include shutter separation, polarization separation, and color separation. In one embodiment, a viewer or user, such as a dentist, can wear viewing glasses to view the separate images with stereopsis and depth perception. In other embodiments, multiple stereoscopic videos can be displayed, such as on multiple television screens. For instance, the stereoscopic image can be simultaneously displayed on a television screen, a projection display, and a head mountable stereoscopic video display.

Certain types of viewing glasses, such as LCD glasses using shutter separation, may be synchronized with the display screen to enable the viewer to view the optically separated near real-time stereoscopic video image. The optical separation of the video feeds provides a visual perception leading to the sensation of depth from the two slightly different video images projected onto the retinas of the two eyes, respectively, to create stereopsis. As previously discussed, the sensation of depth enables the dentist to maintain substantially the same hand-eye coordination that the dentist has learned during his or her practice as a dentist.

The stereoscopic video display 206 can also be used to view information pertaining to the patient. For instance, x-rays can be digitized and viewed on the video display. A patient's chart information can also be displayed. This can enable the dentist to quickly come up to speed on the patient's status. The dentist can also make comparisons between previous images and information contained in the patient's chart and the patient's current status. The images can also be used to educate the patient, dental assistants, and so forth.

In one embodiment, the fixture 242 can be hingeably mounted or otherwise height adjustable. The distance of the video cameras to the patient can be varied as desired. For instance, the video cameras may be positioned at a distance from about 5 inches to about 96 inches above the patient's intraoral cavity. As the distance between the video cameras and the patient changes, the angle at which the first video camera and the second video camera are directed relative to one another can be adjusted to maintain stereopsis of the near real-time stereoscopic video image.

Figure 3:
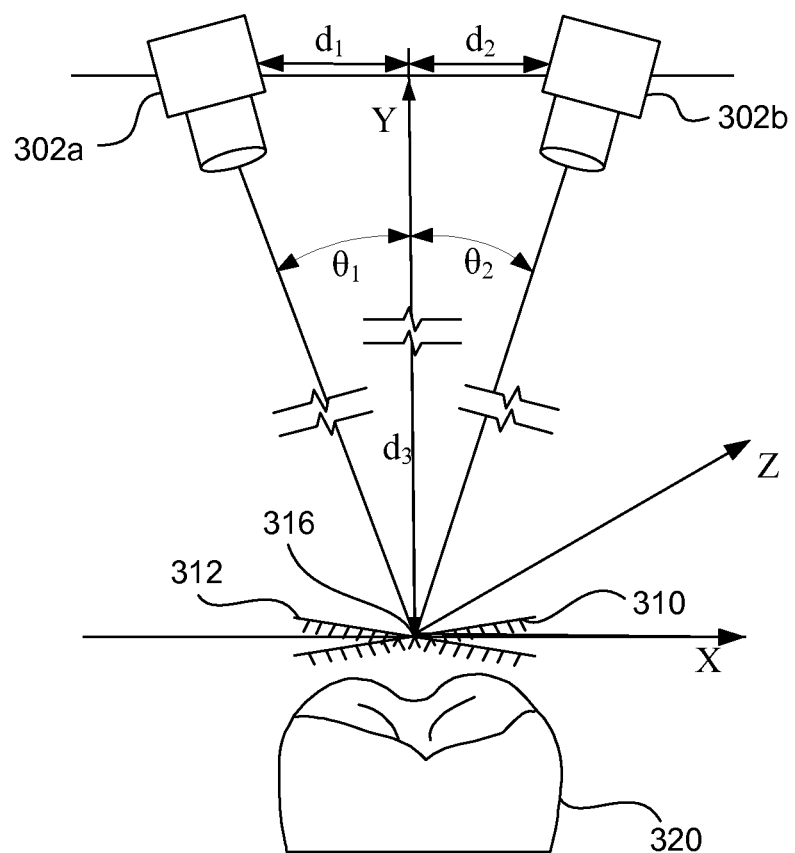
FIG. 3 provides an exemplary diagram illustrating angles at which the first and second video cameras are directed and changed based on a distance of the video cameras from a selected object to maintain stereopsis of the video image in accordance with an embodiment of the present disclosure.

FIG. 3 provides an exemplary diagram illustrating how the angles of the first and second video cameras 302a, 302b are related to a distance from an object. It should be noted that the illustration is not drawn to scale. The cameras can be separated by a selected distance, such as a pupillary distance, as previously discussed. In one embodiment, distance $d_1$ can be substantially equal to distance $d_2$. In this example, $d_1=d_2=30$ mm. However, the actual distance may vary based on system needs, e.g., $d_1+d_2=$a value in the range of about 50 mm to 75 mm.

In order to view a selected object 320 or area, such as a tooth in this example, the first video camera 302a is directed to the object at an angle $\theta_1$ with respect to a normal. The second video camera 302b can be directed to the object at an angle $\theta_2$ with respect to the normal. When the object is centered between the cameras 302a, 302b then $\theta_1$ is substantially equal to $\theta_2$, though this is not necessarily required.

The first video camera 302a can create a video image of a first plane 310, based on the angle $\theta_1$. The second video camera 302b can create a video image of a second plane 312 based on the angle $\theta_2$. The first and second planes 310, 312 cross at a location referred to as a convergent point 316. In one embodiment, the convergent point can be selected to be positioned at approximately the location of the object 320. Alternatively, the convergent point may be selected to be within the depth of field of the cameras. When the image is magnified by zooming the first and second cameras, then the convergent point can be selected such that it is within the final, magnified video image.

As the distance $d_3$ between the cameras 302a, 302b and the object 320 changes, the angles $\theta_1$ and $\theta_2$ can be adjusted such that the convergent point is maintained at approximately the same location. The distance of $d_3$ may change when a position of the fixture 242 of FIG. 2 is adjusted relative to the patient 234. The distance of $d_3$ may also change when the patient moves.

As previously discussed, a tracking point can be used to track movements of the patient. In one embodiment, the convergent point can be separate from the tracking point. For instance, the tracking point may be an optical marker on a patient's forehead and the convergent point can be the focus point on a patient's tooth. The convergent point can be correlated with the tracking point such that when the tracking point moves a certain amount in at least one of the x, y, and z axes, the convergent point can be moved approximately the same distance. Alternatively, the tracking point may be substantially equal to the convergent point. This allows the video feeds of a selected location that are created by the first and second video cameras 302a, 302b to be maintained even when the patient moves, thereby enabling the dentist to maintain a view of the near real-time stereoscopic video image of the selected location.

Returning now to FIGS. 1a-h for purposes of describing actuation of the video cameras, the direction in which the first and second video cameras 102a, 102b are positioned can be updated using at least one electric motor 112 that is mechanically coupled to each video camera. For instance, a single motor may be used to cause an angle of a video camera to be changed along a first axis, such as rotating the video camera. A second motor may be used to allow the video camera angle to be adjusted along a second axis. In one embodiment, two motors are sufficient to allow each video camera to be adjusted along an x and y axis to direct each video camera in a desired direction. However, a third motor may be used to allow the video camera's position to be adjusted along a third axis. The three motors can allow each video camera's position to be redirected along an x, y, and z axis to be directed in substantially any direction.

The at least one motor 112 can communicate with the tracking module 108 to update the position of the first and second video cameras. In one embodiment, a user can manually actuate the position of the first and second video cameras 102a, 102b through the use of a software interface that is in communication with the at least one motor 112.

Once the video cameras 102a, 102b are set in a desired direction, enabling the user to view a selected area, such as a patient's tooth, the location can be set as the convergent point. As previously discussed, the convergent point is associated with a selected tracking point. The position of the tracking point can be selected such that there is about a one to one movement of the tracking point in relation to the convergent point. For instance, an optical marker may be placed on a patient's forehead or somewhere else that is convenient for a given application. When the patient moves his or her head, the change in position of the forehead is generally substantially similar as the change in position of the patient's tooth (barring some sort of unnatural twisting movement that would be less likely while sitting in a dentist chair). Thus, when the tracking point moves, the position of the cameras can be updated relative to the movement of the tracking point to enable the convergent point to be maintained over the same selected area, such as the patient's tooth. The dentist may use an insert, such as a retractor inserted in the patient's oral cavity, so that the angle of opening of the jaw remains substantially unchanged. In one embodiment, when using a retractor, the tracking point can be placed thereon, or on another area close to or within the oral cavity, such as a tooth, lip, cheek, nose, chin, etc. In another embodiment, when using a retractor, such as a cheek retractor, LED or other lighting sources can be included on the retractor. Thus, in embodiments of the present disclosure where an image adjustment module 114 is used (See FIG. 1c), the lighting profile provided by the cheek retractor can be selected for light enhancement or shifting as previously described.

The position of the first and second video cameras 102a, 102b can also be affected by physically changing their location relative to a patient. For instance, the cameras may be mounted on a fixture that can be rotated, raised and lowered, hingeably moved, or otherwise repositioned, as discussed in FIG. 2. When the position of the video cameras are changed by moving the fixture, then the at least one motor 112 can be used to redirect the video cameras to the selected area. In one embodiment, the position of the fixture can be used in conjunction with the motors to direct the video cameras in a desired direction. For instance, a dentist may position the fixture to provide desired lighting and align the video cameras with a patient's intraoral cavity to allow the video cameras to be directed to a desired location within the intraoral cavity.

In other related embodiments, several methods for viewing stereoscopic medical video images are also disclosed. The methods generally include directing a first video camera and a second video camera to a selected area of a subject to generate a respective first video feed and a second video feed of the selected area, wherein the first video camera is separated from the second video camera by a selected distance, and wherein the first video camera and the second video camera are each directed to a convergent point at or near the selected area to provide stereopsis of the selected area. Additional steps include associating the convergent point with a selected tracking point; adjusting a location of the convergent point relative to movement of the selected tracking point; and displaying the first video feed and the second video feed on a display system that optically separates the first video feed and the second video feed to create a near real-time stereoscopic video image.

This general method can also include additional steps. For example, in one embodiment, the step of selecting the first video camera and the second video camera from an array of video cameras can be included. Two cameras of the array can be selected to generate the near real-time stereoscopic image, or a virtual image can be generated using at least one virtual video feed. In this latter embodiment, the method for viewing stereoscopic video images can comprise obtaining an array of video cameras and generating multiple video camera feeds from multiple video cameras of the array. Additional steps include geometrically transforming at least a plurality of the video feeds to create a virtual camera feed; tracking a selected tracking point related to a convergent point; and creating a near real-time stereoscopic video image. The stereoscopic video image can comprise at least two camera feeds, and at least one of the two camera feeds is the virtual camera feed. Furthermore, the at least two camera feeds are typically directed to the convergent point.

In another example, the method can include the step of modifying the near real-time stereoscopic image as a result of a gesture control motion of a user. In another example, the method can include the step of selectively modifying a light signal received by the first video camera and the second video camera, thereby providing a viewable image having at least one adjusted visual property adapted for enhanced diagnostic or treatment visualization by a user. Thus, when displaying the near real-time stereoscopic video image, the adjusted visual property can provide the user, e.g., medical or dental professional, with added information for diagnostics or treatment. In another example, the method can include a calibration module configured to calibrate and adjust horizontal alignment of the first video feed and the second video feed. In still another embodiment, the method can include the step of generating a 3-D model from at least one frame of the near real-time stereoscopic video image.

Regarding the step of directing the first video camera and the second video camera to a selected area of a subject to generate a respective first video feed and a second video feed of the selected area, it is noted that the first video camera can be separated from the second video camera by a selected distance. In one embodiment, the selected distance can be a pupillary distance, or alternatively, a different distance may be selected, as previously discussed, e.g., distances that simulate the pupillary distance by using appropriate angles, or adjusting the images using a processing step. Typically, the first video camera and the second video camera are each directed to a convergent point at or near the selected area to provide stereopsis of the selected area.

These methods can further comprise associating the convergent point with a selected tracking point on or about a subject. The selected tracking point can include an optically trackable marker, as has been discussed. In one embodiment, the optically trackable marker may be positioned on a dental retractor located in or about the patient's intraoral cavity. Alternatively, the selected tracking point can include a plurality of wireless transceivers configured to triangulate a position of the selected tracking point based on the timing of signals received at a transceiver located at the tracking point relative to at least two other transceivers positioned on or about the patient.

For instance, in one embodiment, a surgical operating room may include four separate radio frequency transceivers positioned at different locations about the operating room. A tracking transceiver can then be placed on a patient entering the operating room. The tracking transceiver can send or receive signals from the transceivers located in the operating room. The timing of the signals between the tracking transceiver and the four transceivers in the operating room can be used to determine the position of the tracking transceiver in three dimensions using trigonometry, as can be appreciated. The accuracy of the triangulation calculation is based, at least in part, on the frequency of the transceivers. Higher frequency transceivers have shorter wavelengths, thereby enabling a more accurate determination of the position of the tracking transceiver. Increased accuracy can also be obtained by merely tracking the change in movement. As the tracking transceiver moves closer to one of the transceivers in the room, and further from another, the resulting change in the timing of the signals can enable a substantially accurate determination of the change in position of the tracking transceiver.

The methods further comprise adjusting a location of the convergent point relative to movement of the selected tracking point. In one embodiment, the convergent point can be selected as a virtual point that has an x, y, and z axis distance from the tracking point. When the tracking point is moved then the first video camera and the second video camera can be redirected to maintain a view of the selected area based on the change in the x, y, and z axis distance of the tracking point. For instance, once the convergent point has been selected relative to the tracking point, the tracking point may move 1 inch in each of the x, y, and z axes due to a movement of the patient on which the tracking point is located. It can be assumed that the convergent point has also been moved 1 inch in each of the x, y, and z axes and the position of the first and second video cameras can be redirected to the adjust the location of the convergent point to the new location.

The methods may further include displaying the first video feed and the second video feed on a display system that optically separates the first video feed and the second video feed to create a near real-time stereoscopic video image. In one embodiment, the first video feed can be displayed on a right video display of a head mountable video display and the second video feed can be displayed on a left video display of the head mountable video display. The right and left video displays can be projected onto a user's right and left eyes, respectively. The stereoscopic video image provides a visual perception leading to the sensation of depth from the two slightly different video images projected onto the retinas of the two eyes.

Alternatively, the first video feed and the second video feed can be displayed on a single display wherein the first video feed and the second video feed are optically separated using at least one of shutter separation, polarization separation, and color separation, as previously discussed. Depending on the type of optical separation used, glasses may be used to enable a user to separate the image displayed on the single display to the first video feed being directed to the user's right eye and the second video feed being directed to the user's left eye, or vice versa.

The first video camera and the second video camera can each be zoomed to provide a desired level of magnification of a selected portion of the near real-time stereoscopic image. The rate at which the magnification changes for each of the first and second video cameras can be substantially equal to maintain the stereopsis of the stereoscopic video image. The final amount of magnification can also be substantially equal for the same reason. In addition to optically magnifying the stereoscopic video image using the first and second cameras, the video image can be further magnified using digital magnification, as can be appreciated.

In discussing the systems and methods of the present disclosure above, is also understood that many of the functional units described herein have been labeled as "modules," in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A system for generating stereoscopic video images, comprising:
   an array of video cameras configured for providing video feeds of an object;
   an image processor configured to:
      receive video feeds from the array,
      geometrically transform one or more of the video feeds to create a virtual video feed that presents a virtual perspective which is an interpolation of one or more of the video feeds, and
      generate a stereoscopic video image from at least two video feeds, wherein at least one of the two video feeds is the virtual video feed, and wherein the two video feeds are directed to a convergent point; and
   a tracking device associated with the array, the tracking device configured to follow a tracking point relative to the convergent point in order to maintain stereopsis, wherein movement of the tracking point causes corollary movement of the convergent point in at least one of an x, y, or z, axis, and wherein the tracking device causes the at least two video feeds to be directed to the convergent point.

2. The system of claim 1, wherein the tracking point is associated with movement of the object.

3. The system of claim 1, wherein a sensor is associated with the tracking device, and wherein the tracking point follows a movement of a user.

4. The system of claim 1, further comprising a zooming device associated with the video cameras, the zooming device configured to provide a magnification of the stereoscopic video image.

5. The system of claim 1, wherein the image processor is further configured to selectively modify one or more of the two video feeds to provide a stereoscopic viewable image having at least one adjusted visual property adapted for enhanced diagnostic or treatment visualization, and wherein the adjusted visual property includes enhancement of a specific color or group of colors.

6. The system of claim 1, wherein the system further comprises a video display adapted to create stereopsis, comprising:
   a single video screen wherein the two video feeds are optically separated using at least one of shutter separation, polarization separation, or color separation; or
   a right eye display and a left eye display associated with the two video feeds for viewing by a user's right eye and left eye, respectively.

7. A system for generating stereoscopic video images, comprising:
   a first video camera configured to generate a first video feed of an object;
   a second video camera configured to generate a second video feed of the object, wherein the first video feed and the second video feed are combined to generate a stereoscopic video image;
   a tracking device associated with the first video camera and the second video camera, the tracking device configured to cause the first video camera and the second video camera to be directed to a convergent point relative to a tracking point to maintain stereopsis wherein movement of the tracking point causes corollary movement of the convergent point in at least one of an x, y, or z, axis; and
   a gesture control device with sensors associated with the system, wherein the sensors sense a movement of the user and the system responds based on the movement of the user, wherein the gesture control device is configured to adjust at least one of an angle or a magnification of the first and second video cameras to adjust the stereoscopic video image based on a movement of the user.

8. The system of claim 7, wherein the movement is a deliberate hand, arm, voice, head, eye, or instrument gesture.

9. The system of claim 7, wherein the first video camera and the second video camera are spatially separated at a pupillary distance from one another.

10. The system of claim 7, wherein the tracking device maintains stereopsis as movement occurs relative to the tracking point, the first video camera, or the second video camera.

11. The system of claim 7, further comprising a processor configured to calibrate and adjust a horizontal alignment of the first video camera, the second video camera, or both.

12. The system of claim 11, wherein the processor provides for calibration with multiple users, and wherein the system calibrates to a first user in a first mode and a second user in a second mode.

13. The system of claim 11, wherein the horizontal alignment is maintained during pan or tilt movements of one or more of the video cameras.

14. The system of claim 7, further comprising a zooming device associated with the first video camera and the second video camera, the zooming device configured to provide a magnification of the stereoscopic video image.

15. The system of claim 7, wherein the system further comprises a video display adapted to create stereopsis, comprising:
   a single video screen wherein the first video feed and the second video feed are optically separated using at least one of shutter separation, polarization separation, or color separation; or
   a right eye display and a left eye display associated with the first video feed and the second video feed, respectively.

16. The system of claim 7, adapted for use in a dental setting, wherein the object is an intraoral cavity.

17. The system of claim 7, further comprising a processor configured to selectively modify one or more of the video feeds to provide a stereoscopic viewable image having at least one adjusted visual property adapted for enhanced diagnostic or treatment visualization, wherein the adjusted visual property includes enhancement of a specific color or group of colors, wherein the specific color or group of colors is enhanced for diagnosing or treating cancers or lesions in the mouth, or wherein the processor is configured to enhance the display of a colorant in the stereoscopic video image.

18. The system of claim 7, further comprising a processor configured to convert an image generated from the stereoscopic video image into a 3-D model or construct.

19. The system of claim 7, wherein the first video camera and the second video camera are part of an array of video cameras including at least three spatially separated video cameras each configured to generate a video feed of an object, the plurality of video cameras adapted so that multiple pairs of video cameras are capable of generating a stereoscopic video image, each of the pairs of video cameras configured to generate a pair of video feeds relative to the object, and the tracking device is associated with the array of video cameras, the tracking device configured to cause pairs of video cameras to be directed to a convergent point relative to the tracking point to maintain stereopsis.

20. A method of generating stereoscopic video images, comprising:
   directing a first video camera and a second video camera at an object to generate a first video feed and a second video feed, wherein the first video camera is separated from the second video camera by a selected distance, and wherein the first video camera and the second video camera are each directed to a convergent point at or near the object to provide stereopsis; associating the convergent point with a selected tracking;
   adjusting a location of the convergent point relative to movement of the selected tracking point, wherein movement of the tracking causes a corollary movement of the convergent point in at least one of an x, y, or z axis, and the location of the convergent point is adjusted by modifying a direction of the first video camera or the second video camera;
   displaying the first video feed and the second video feed on a display system, comprising:
      a single video screen wherein the first video feed and the second video feed are optically separated, or
      a right eye display and a left eye display associated with the first video feed and the second video feed, respectively; and
   modifying the stereoscopic image as a result of a gesture control motion of a user, wherein the gesture control motion is configured to adjust at least one of an angle or a magnification of the first and second video cameras to adjust the stereoscopic video image based on a movement of the user.

* * * * *